United States Patent
Vogtmeier et al.

(10) Patent No.: US 11,179,117 B2
(45) Date of Patent: Nov. 23, 2021

(54) X-RAY MISUSE PROTECTION

(71) Applicant: KONINKLIJKE PHILIPS N.V., Eindhoven (NL)

(72) Inventors: Gereon Vogtmeier, Aachen (DE); Ravindra Bhat, Eindhoven (NL); Biswaroop Chakrabarti, Kolkata (IN); Prasad Raghotham Venkat, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 21 days.

(21) Appl. No.: 16/623,476

(22) PCT Filed: Jun. 20, 2018

(86) PCT No.: PCT/EP2018/066362
§ 371 (c)(1),
(2) Date: Dec. 17, 2019

(87) PCT Pub. No.: WO2019/002039
PCT Pub. Date: Jan. 3, 2019

(65) Prior Publication Data
US 2020/0113530 A1    Apr. 16, 2020

(30) Foreign Application Priority Data
Jun. 27, 2017  (EP) .................................... 17178055

(51) Int. Cl.
*A61B 6/10* (2006.01)
*A61B 6/00* (2006.01)

(52) U.S. Cl.
CPC .............. *A61B 6/10* (2013.01); *A61B 6/4405* (2013.01); *A61B 6/548* (2013.01); *A61B 6/545* (2013.01)

(58) Field of Classification Search
CPC ......... A61B 6/10; A61B 6/4405; A61B 6/548; A61B 6/545; A61B 6/544; A61B 6/588; A61B 6/54; A61B 6/46; A61B 6/467
(Continued)

(56) References Cited

U.S. PATENT DOCUMENTS

| | | |
|---|---|---|
| 2009/0024053 A1 | 1/2009 | Kasahara |
| 2009/0238493 A1 | 9/2009 | Crucs |

(Continued)

FOREIGN PATENT DOCUMENTS

| | | |
|---|---|---|
| CN | 2735934 Y | 10/2005 |
| CN | 103340646 A | 10/2013 |

(Continued)

OTHER PUBLICATIONS

PCT International Search Report, International application No. PCT/EP2018/066362, dated Oct. 26, 2018.

*Primary Examiner* — David P Porta
*Assistant Examiner* — Gisselle M Gutierrez
(74) *Attorney, Agent, or Firm* — Larry Liberchuk

(57) ABSTRACT

An apparatus (M) and related method for supporting X-ray imaging. The apparatus comprises an input interface (IN) for receiving a request to perform an X-ray exposure with an X-ray source (XR) of an X-ray imager (XI) to image an object (PAT). A compliance checker (CC) of the apparatus (M) is configured to check said request against an imaging safety protocol for said object to produce a safety compliance result. A safety enforcer (SE) of the apparatus is configured to issue, based on the safety compliance result, i) an alert signal and/or ii) a control signal to initiate a safety action that at least affect an impact of the requested X-ray exposure on the object.

12 Claims, 3 Drawing Sheets

(58) Field of Classification Search
USPC .......................................................... 378/62
See application file for complete search history.

(56) References Cited

U.S. PATENT DOCUMENTS

| | | | |
|---|---|---|---|
| 2013/0089176 A1* | 4/2013 | Nabatame | A61B 6/461 |
| | | | 378/8 |
| 2013/0279644 A1* | 10/2013 | Yanagida | A61B 6/032 |
| | | | 378/8 |
| 2014/0304206 A1 | 10/2014 | Lee | |
| 2017/0199979 A1* | 7/2017 | Reiner | G16H 20/40 |
| 2020/0187877 A1* | 6/2020 | Chakrabarti | A61B 6/542 |

FOREIGN PATENT DOCUMENTS

| | | |
|---|---|---|
| CN | 204330632 U | 5/2015 |
| JP | 20110139761 A1 | 2/2013 |
| WO | WO2014033614 A1 | 3/2014 |
| WO | WO2016079047 A1 | 5/2016 |

* cited by examiner

X-RAY MISUSE PROTECTION

FIELD OF THE INVENTION

The invention relates to an apparatus for supporting X-ray imaging, to an imaging system, to a method of supporting X-ray imaging, to a computer program element, and to a computer readable medium.

BACKGROUND OF THE INVENTION

Mobile X-ray systems for diagnostic imaging are set to become an attractive solution for rural areas, or in other low-cost settings, but also for areas with high population density, or in nursing homes, etc.

However, the question to ensure safe operation remains. For instance, usage of such X-ray system by poorly trained staff may not be uncommon in such settings and may result in health risks to patients and others, due to unwanted radiation caused by incorrect usage of the X-ray system. X-ray systems use ionizing radiation which could be extremely dangerous when a person is radiated with too high a dose. This misuse could be due to multiple X-ray exposures in a short period of time, which were actually unwarranted medically.

SUMMARY OF THE INVENTION

There may therefore be a need for systems and method to reduce the risk of misuse of X-ray imagers.

The object of the present invention is solved by the subject matter of the independent claims where further embodiments are incorporated in the dependent claims. It should be noted that the following described aspect of the invention equally applies to the imaging system, to the method of supporting X-ray imaging, to the computer program element, and to the computer readable medium.

According to a first aspect of the invention there is provided an apparatus for supporting X-ray imaging, comprising:

an input interface for receiving a request to perform an X-ray exposure with an X-ray source of an X-ray imager to image an object;

a compliance checker configured to check said request against an imaging safety protocol for said object to produce a safety compliance result, wherein the checking by the compliance checker is based on information that identifies the object, wherein the imaging safety protocol prescribes a maximum number of allowable X-ray exposures for the so identified object; and a safety enforcer configured to issue, based on the safety compliance result, i) an alert signal and/or ii) a control signal to initiate a safety action that at least affects an impact of the requested X-ray exposure on the object.

References herein to "the object" shall be construed to include animate and inanimate objects. Main reference of "object" is to be construed as a human or animal patient in a medical context is mainly envisaged herein. However, non-medical contexts with inanimate objects are not excluded herein, such as when imaging inanimate objects that are easily damaged by X-ray, such as in luggage screening or non-destructive material-testing or other.

The information on the identity of the object (in particular of the patient) may be included in the request, may be provided in addition by a user (operator) of the imaging apparatus or may be provided by a sensor system. The maximum number of allowable X-ray exposures may differ from patient to patient. For instance, the said number may be lower for a child than for an adult. The number may be as low as one, or two, or three, four, five, 10, or any other suitable number>0.

According to one embodiment, said safety action includes any one or a combination of i) locking down or shutting down the X-ray imager ii) adjusting a setting of the X-ray source, including reducing a voltage or a current of the X-ray source or an exposure time, or iii) operating a collimator of the X-ray imager to change (eg, reduce or increase) X-ray exposure, iv) performing a relative motion between object and X-ray source.

The "locking down" action may include in particular disabling the X-ray source whilst maintaining power supply for the imager as a whole.

The adjusting of the voltage or amperage or exposure time is preferably to reduce dose on the patient. This can be achieved by reducing the voltage or current of the X-ray source. In other use scenarios, in order to ensure a pre-set image quality, the safety action may include increasing voltage or current or exposure time. Image quality (eg, contrast) can be quantified by a number of different metrics, including SNR (signal-to-noise ratio) and others. The dose should be as low as possible to still achieve the (pre-set) image quality. Equally, the collimator may be operated to reduce X-ray exposure if dose is higher than necessary as per the safety protocol, but, in other cases, an increase of X-ray exposure may be called for to ensure a preset image quality, whilst keeping dose within pre-set bounds.

According to one embodiment the apparatus comprises a protocol changer configured to change said safety protocol in response to receiving further information on said object or on a change in relation to said object. This further information includes in one embodiment any one of i) a height or ii) a body mass or iii) a change of position of said object or iii) a change of identity of said object. This can help avoid X-ray exposures with no diagnostic value. Once the protocol changer changes the safety protocol, the safety checker re-checks for compliance.

According to one embodiment said further information or the information that identifies the object is provided by one or more sensors that are operative to perform one or more measurements in relation to said object.

In other words, the protocol changer implements a configurable safety protocol that defines the way how the X-ray system is used and also how it should not be used. In the protocol, different degrees of control-level could be defined and depending on information captured (e.g., what type of sensor is used) it would be possible to start an X-ray acquisition or not. Amongst others, a limiting parameter for an imaging setting encodable in the proposed protocol is, preferably explicitly, the number of allowed X-ray shots per patient. This would help avoid too many exposures for the same patient, and hence risk of misuse can be reduced. More specifically, and according to one embodiment the imaging safety protocol prescribes any one or a combination of i) number or exposure per unit time, ii) maximum or minimum voltage of the X-ray source. The safety protocol may also prescribe the maximum dose and the minimum image quality required.

According to one embodiment the apparatus comprises a user interface for receiving said further information or the information that identifies the object from a user.

According to one embodiment the apparatus comprises a communication interface for receiving said further information of the information that identifies the object from a remote data supplier equipment.

According to a second aspect there is provided an imaging system, comprising:

an apparatus as according to any one of the above described embodiments and an X-ray imager.

According to a third aspect there is provided a method of supporting X-ray imaging, comprising the steps of:

receiving a request to perform an X-ray exposure with an X-ray source of an X-ray imager to image an object;

checking said request against an imaging safety protocol for said object to produce a safety compliance result, wherein the checking is based on information that identifies the object, wherein the imaging safety protocol prescribes a maximum number of allowable X-ray exposures for the so identified object; and issuing, based on the safety compliance result, i) an alert signal or ii) a control signal to initiate a safety action that at least reduces an impact of the requested X-ray exposure on the object.

According to one embodiment, the method further comprises changing said safety protocol in response to receiving further information on said object or on a change in relation to said object.

According to a fourth aspect there is provided a computer program element, which, when being executed by at least one processing unit, is adapted to perform the method as per any of the embodiments described herein.

According to a fifth aspect there is provided a computer readable medium having stored thereon the program element.

The proposed system and method could be used in mobile healthcare systems like (ultra-)mobile X-ray systems, but the method could be applied also for other X-ray devices, such as fixed system, C-arm or CT scanner, etc.

"X-ray exposure" relates to manners in which the X-radiation is allows to impact on the patient. The exposure relates to the dose received or receivable by the patient and is a function in particular of an X-ray source setting (voltage, amperage and/or time/duration).

"Imaging request" are one or more commands with associated imaging settings for an imaging procedure. The request is either manually supplied by a user/operator (e.g., health professional), or are automatically supplied, possibly repeatedly, for instance within the course of an unfolding imaging procedure where multiple exposures are required. The imaging request may also relate to an on-going imaging event. In other words, the imaging request may not necessarily constitute an instantaneous event but may constitute an event that is maintained for at least as long the requested imaging procedure is on-going.

"Safety" of usage includes ensuring patient is not receiving too much dose relative to a given image quality to be achieved. Hence, enforcing safety may also mean in certain circumstances to increase dose to ensure image quality if dose still remains within pre-defined bound as per the safety protocol. Producing imagery with too low image quality may be of no or little diagnostic so the corresponding dose, low as it may be, was received at the patient with no or little benefit.

Radiation" or "scatter" should be interpreted herein as references to X-radiation and scattered X-ray radiation, respectively.

"X-radiation" is shorthand for X-ray radiation.

"Imager" as used herein is short hand for the whole X-ray imaging apparatus.

BRIEF DESCRIPTION OF THE DRAWINGS

Exemplary embodiments of the invention will now be described with reference to the following drawings (which are not to scale) wherein.

DETAILED DESCRIPTION OF EMBODIMENTS

Figure 1:
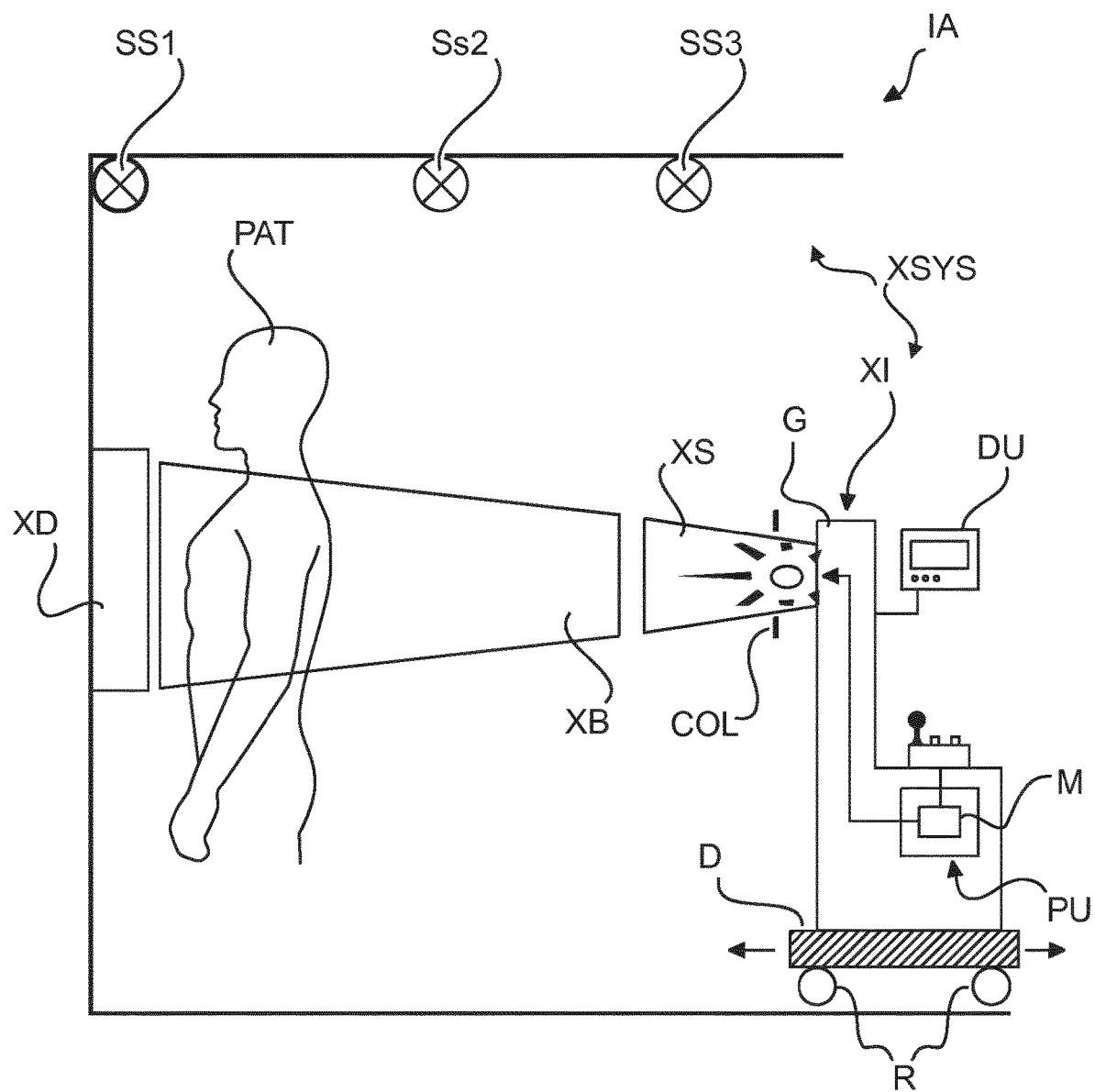
FIG. 1 shows a block diagram of an X-ray imaging system.

With reference to FIG. 1, there is shown an imaging arrangement IA. The arrangement includes an X-ray imager XI and a system XSYS comprising safety module M (referred to herein as "the module") that supports safe operation of the X-ray imager in a manner to be described in more detail below.

The X-ray imager XI as mainly envisaged herein is of the mobile or portable type. One such embodiment of a mobile X-ray imager XI is shown schematically on the bottom right of FIG. 1.

The X-ray imager XI is mobile or portable in the sense that it can be moved from one location, such as from an examination room RM, to another location, in particular to another examination room. This is particularly useful in settings where it is impractical to have a dedicated examination room. The imaging can advantageously be performed in any room that happens to be vacant at a given time. Preferably, there is no disassembling required when moving the mobile imager XI to the other usage location. The mobile X-ray imager IA as envisaged herein in one embodiment includes a dolly D or undercarriage with rollers R. Erected on said moveable undercarriage is a gantry G that holds the X-ray source XS.

The X-ray imager further includes an X-ray sensitive detector XD, preferably of the digital type, in particular in flat-panel technology. The X-ray tube XS is arranged preferably moveably on the gantry G so that tube XS can be aligned with the X-ray detector XD. Alternatively, the source XS is fixed and the detector XD is movable on a fixture for alignment with the X-ray source XS.

In the mobile embodiment shown in FIG. 1, there is no physical or structural connection between the X-ray detector XD and the remainder of the X-ray imaging apparatus. In particular, the X-ray detector XD is not mounted on an arm of the gantry although this may still be so in other, alternative embodiments. More compact, portable, solutions as the one shown in FIG. 1 are also envisaged in alternative embodiments, for instance for use in ambulance vehicles. In these portable embodiments, the X-ray imager XI may not necessarily include rollers R but is compact and light enough to be carried (possibly in a suitable carrying case) from the ambulance to the incident site. The X-ray source XS and/or the detector XD of the imager XI may be releasably mountable in suitable fixtures arranged inside the vehicles, e.g. on the vehicle's cabin wall for instance. "Vehicles" as envisaged herein include not only land travelling vehicles (cars, vans, etc) but also aircraft (helicopters, airplanes) or ships. Although mobile or portable imaging systems are mainly envisaged herein, this is not at the exclusion of other traditional, fixed settings such as C- or U-arm X-ray imagers or CT scanners, etc. The X-ray imager XI may be powered by an external power supply through a power cord connected to a power output, or the imager XI may have an autonomous on-board energy source such as batteries.

The X-ray imager XI further includes an operator console OC that allows the user to perform various control functions such as configuring various imaging settings or parameters and starting X-ray exposure for imaging. The operator console OC is implemented as functionalities of an on-board computing unit PU. Alternative embodiments are also envisaged where the computing unit PU is outsourced to remote server system, communicatively coupled to the imager XI.

The configurable imaging settings include in particular the X-ray source ("tube") XS settings. The tube settings include voltage or current at which the X-ray source is to be operated for an imaging session and hence the energy of the X-radiation so produced, specifiable in keV and/or the duration of exposure and/or the frequency of the exposure, and other parameters. The imaging settings may also include the imaging geometry. The imaging geometry relates to the mutual geometrical configuration of the patient PAT relative to source and detector. The imaging geometry also includes the "SID" distance (distance between source XS and detector XD). The imaging settings may be configured by a suitable user interface UI (textual or graphical) of the operator console OC.

The user can further input, by said user interface UI or a different user interface, patient characteristics, in particular sex, height, weight, age, patient ID (identification information (e.g. patient number) that allows establishing the specific identity of the patent PAT to be imaged, etc.

The user may select some or all the imaging settings directly or indirectly by choosing an imaging protocol that prescribes appropriate, and in most cases mandatory, imaging settings that match the patient characteristics.

In other words, the imaging settings as per the image protocol are in general a function of i) the patient characteristics and the imaging task to be performed on the patient PAT. The imaging task defines the purpose of the imaging, in particular the organ or body part to be imaged. The imaging protocol ensures a certain image quality and is designed to ensure the patient dose/exposure is as low as possible. The exemplary embodiment in FIG. 1, shows a set up for a lung or chest imaging procedure. In this particular example, the patient PAT is required to stand whilst in other imaging situation patient PAT lies on an examination table (not shown) arranged between X-ray source XS and detector XD.

Instead of adjusting manually some or all of the patient characteristics and/or the imaging setting or instead of selecting manually the imaging protocol by the user through the UI as described above, the patient characteristics and/or the imaging setting and/or the imaging protocol may be adjusted or selected automatically, e.g. through the computing unit PU by retrieving patient data through a network (not shown) from a data source (e.g., electronic health record) and then matching same to data in a medical knowledge database DB to find the appropriate imaging settings/imaging protocol. The imaging protocol is preferably specified in a machine readable format, such as XML, DICOM or other.

The X-ray source XS includes in general an evacuated tube. Inside the tubes there are arranged an anode and a cathode. The cathode is usually a rotating disc. When power is applied across the anode and the cathode, electrons are emitted from the cathode and accelerated from the cathode towards the anode. Upon impact of the election beam at a focal spot on the cathode disc, X-radiation is produced which exits the X-ray housing of the X-ray source through an exit window towards the patient PAT and the X-ray detector XD. In other words, the patient PAT or the body or organ of interest is arranged in a space between the X-ray source XS in particular at its focal spot and the detector XD. Yet more particularly, the electron beam emitted from the cathode impacts the rotating anode disc at a focal spot from which the X-radiation is emitted towards the patient PAT.

The X-radiation so generated exits the X-ray housing in form of a primary beam XB which may be suitably collimated by a collimator COL. The collimated X-ray beam is usually of cone, pyramidal or fan shape, depending on the imaging technology used. The collimator allows adjusting a width of the primary X-ray beam. In particular, the collimator can decrease the cross-section of the beam XB. Collimator settings may be user adjustable through the operator console OC and/or may form further imaging settings prescribed in the imaging protocol.

The primary X-ray beam XB is formed from streams of photons, and the volume flooded by said primary X-ray beam corresponds to all trajectories along which photons can ideally travel. When there is no patient PAT in the beam, these trajectories are straight geometric lines that extend from the focal spot to different pixel positions of the detector XD. However, when patient PAT resides between X-ray source XS and detector XD, photons travel through tissue. The photons then interact with patient tissue of, in general, different type and density (bone, fat, muscle, etc). This interaction includes in particular attenuation. In other words, the intensity with which the photons are registered by radiation sensitive pixels PX of the detector XD at the far end of the patient is decreased, compared to the intensity the photons had prior to impacting the tissue. The intensity variations detected at the detector, at least partially, correlate with structural features, in particular density of the tissue. In other words, the structural density variations are modulated onto the intensity variations and this confers image contrast. The detected intensity variations can then be used to form digital images of internal anatomy of the patient. Specifically, photons that impinge on the detector surface after travelling through the patient cause, according to their intensity, an electric signal at respective pixels. These electrical signals ("raw data") are then together processed by a suitable AD-conversion unit into digital image signals. The digital imaging signals are transmitted via a wired or wireless connection communication network to the processing unit PU where imaging processing software is run and where the images are then produced. The images can then be displayed on a display unit DU. The display unit DU is preferably part of the X-ray imager XI but this may not be so necessarily in all embodiments. The displaying of the images may be affected in real time. Instead of, or in addition to, displaying the images, these may are transferred via wired or wireless communication network into storage for further processing or later review.

Useful as X-radiation may be for X-ray imaging, it has also negative side effects and can cause serious health risks. Unnecessary exposure of humans or animals to X-radiation, in particular with scatter x-radiation, should be avoided. It is then proposed herein to foster safer operation of the X-ray imager XI by providing a system XSYS.

This "misuse" protection system XSYS includes in particular a safety module M (referred to herein as "the module"). The module is operative to make the X-ray imager XI safer to use, in particular for inexperienced or overworked staff/user.

Broadly, the proposed module M uses the above mentioned safety protocol (referred to herein also as "the protocol") that defines typical and safe X-ray usage as function of patient characteristics and intended imaging task. The module takes into account the specific characteristics of patient PAT to be imaged.

The safety protocol as proposed herein includes in particular, in on embodiment, the maximum number of X-ray exposures permissible for the given patient PAT per unit time (e.g. per day or per week), based on the patient characteristics. Imaging settings for a planned or currently on-going imaging procedure are compared by a compliance checker CC of module M to the requirements in the safety protocol. If a violation is detected, that is, if the requested imaging settings are not in compliance with the requirements as laid out in the safety protocol, an alert signal is issued and/or safety restoring action is effected by the module M. "Safety action" may include intrusive measures such as to lock down or shut-down the imaging apparatus IA. A lock-down includes disabling an essential component of the imager XI, in particular the X-ray source XS. When in lock-down, the imager remains powered-up however. This is unlike a shut-down where power to the whole imager XI is cut through a switch, etc. Alternatively, less intrusive actions such as re-collimation or tube-voltage change (eg reduction) may also be envisaged instead, or as pre-actions before any one of the more intrusive actions are effected. In embodiments, if the intended or requested imaging task includes an intended X-exposure and if this would result in exceeding the set maximum number of X-ray exposures, the safety action is performed. For instance, the safety action initiated by the module M may prevent that the intended X-ray exposure occurs. The safety action may be any single one or a combination of any one the above described safety action embodiments. In addition or instead, the alert signal issues.

Figure 2:
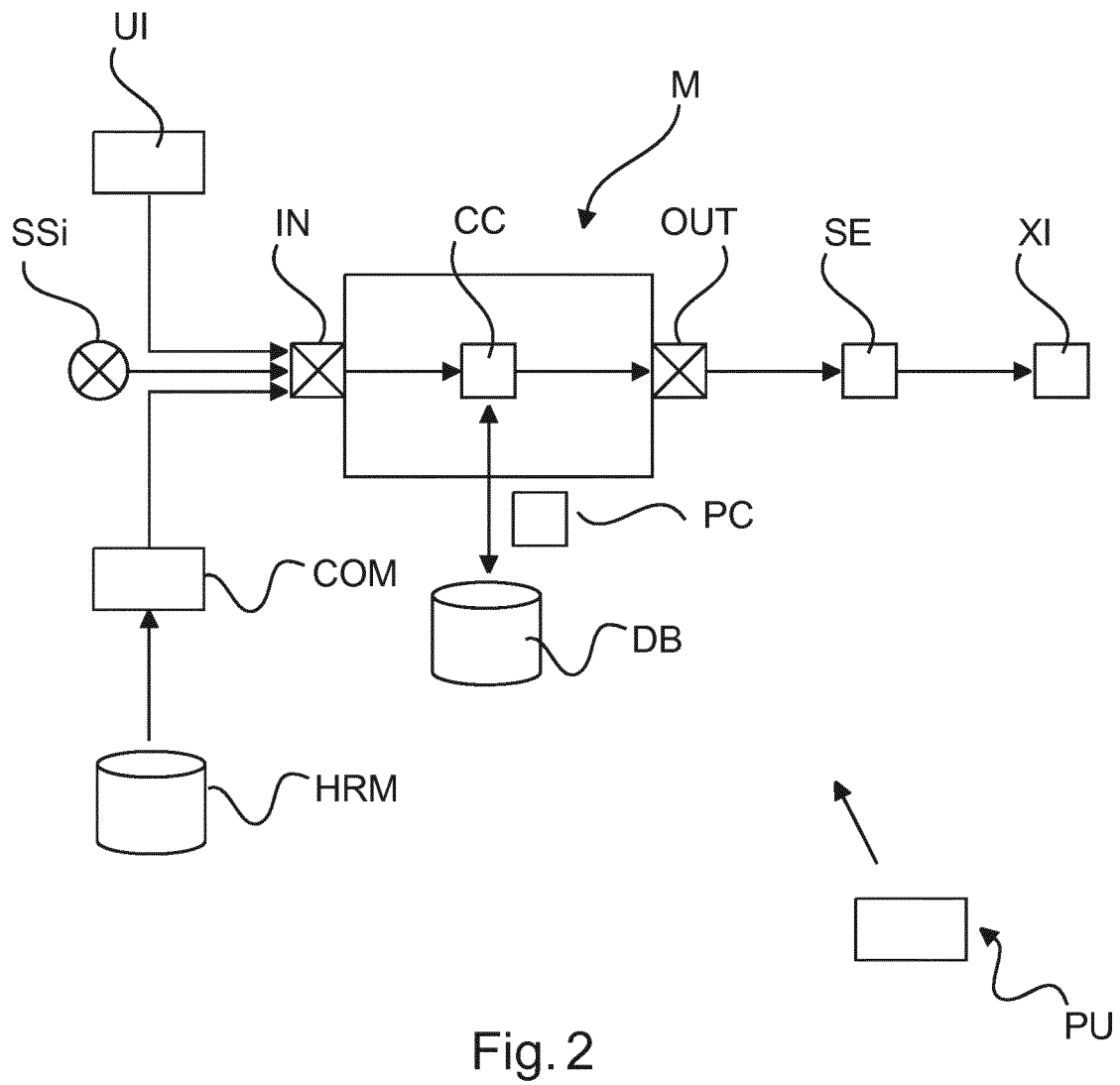
FIG. 2 shows a more detailed block diagram of the module used in the system of FIG. 1.

Turning now to FIG. 2, this shows a block diagram of the proposed safety module M. It includes an input port IN and an output port OUT. At input port IN, an imaging request is received at said input port IN. The image request is associated with the imaging settings currently in use or which the user intends to use. The compliance checker CC matches the received imaging settings associated with the request against the requirements encoded in the safety protocol. The compliance checker CC operates preferably automatically without user approval or interaction to ensure safe X-ray usage. The safety protocol may be retrieved from a data base DB remotely or onboard. The safety protocol may be encoded in a suitable data format and/or data structure such as parameters or ranges of parameters (e.g., interval of permissible keV values) in fields of a database or in entries of nodes of a mark-up language file such as XML or other. Suitable formats also include DICOM. In dependence on this check, an output signal is issued and output at output port OUT.

More specifically, if a violation is detected, an alert signal and/or a control signal is issued. The alter signal may include actuating a suitable transducer such as a loudspeaker to issue an audio alarm signal and/or it may include using an optical transducer such as flashing a light arranged in an examination room or on the imager XI. However, issuing an alert signal as envisaged herein may also include effecting sending a message through suitable communication channel such as via text, email, etc. to a receiver unit. The receiver unit may be a hand held device or a stationary fixed computer of senior staff. The message will allow senior staff to review the extent or nature of the violation detected by the compliance checker. Senior staff member may then ask the user for a consultation or senior staff member may issue a release signal so as to re-enable the imaging apparatus XI if the detected violation is deemed to be not too severe in the circumstances. The message sent to the senior member as envisaged above may also include sending some or all of the patient characteristics, and a selection or all of the imaging settings the user intended to use or which he has used. The message may include all or a selection of the safety protocol, preferably including a mark-up to indicate where in the protocol the violation is deemed to have occurred.

The control signal may be issued together with the alert signal or may be issued instead of the alert signal. The control signal initiates a safety action. The control signal is passed on to the safety enforcer SE. The safety enforcer SE includes all the necessary interfaces and/or middleware etc. to translate the alert signal received from the compliance checker into respective actuator control signals for hardware components such as: the power supply of the X-ray source; the main power supply of the imager XI or the collimator COL of the imager XI, etc. so as to be able to effect the relevant actions such as lock-down/shut-down of the imager XI. To this end, the safety enforcer includes a look-up table component. In the look-up table, types or nature of violations are assigned to respective actions. The look-up table may be used to match violation as detected by checker CC to safety action to be effected by enforcer SE. The safety enforcer SE may be configured to implement a cascaded action sequence. The actions occur in sequence according to severity of the violation detected by compliance checker CC. More intrusive actions are applied only if earlier less intrusive actions in the sequence have failed to restore safety. For example, first a re-collimation is attempted but if this fails to satisfy the safety protocol due to other changes occurring in relation to the patient, the safety enforcer moves on to apply more intrusive actions, such as lock-down or even shut-down of the imager, the latter action being the most intrusive one.

The imaging request received at input port IN includes, or at least references, patient characteristics: like, in particular, weight or height, sex, age. Instead or in addition, it includes patient identification information such as name, a health insurance number or other identity (ID) number, etc. that allows establishing the identity of the patient to be imaged. Patient characteristics may be explicitly supplied by the user through the user interface UI. The user interface UI may allow inputting the patient characteristics and imaging task (e.g., chest X-ray as exemplary shown in FIG. 1) either graphically or text based. In one embodiment, the X-ray imager may include as the user interface UI a touch screen/display screen DU integrated into the operator console OC where the user can conveniently specify the patient characteristics and/or the imaging task to be performed.

In addition or instead, the imaging request may be indirectly input. To this end, the module M includes a suitable network communication interface COM to interface through a network with a health record memory HRM (such as a database) to retrieve the necessary patient characteristics, using for instance the above mentioned patient ID as a query key.

The patient characteristics may also be inferred by using a sensor systems $SS_i$ with one or more sensors. Three such sensors SS1-SS3 are shown mounted in the examination room, but this number is exemplary. The expression "$SS_i$" may be used in the following for the sensor system collectively, irrespective of how many sensors are deployed.

Generally, the sensor system $SS_i$ is configured to gather patient characteristic data which are then supplied to input port IN to retrieve or configure the imaging safety protocol. The image characteristics gathered by the sensor system $SS_i$ is automatically forwarded to input port IN through a wired or, preferably, wireless connection, and is linked to the current imaging request, in particular to the currently used safety protocol. A number of different embodiments are envisaged for the sensor system $SS_i$.

According to one embodiment the sensor system $SS_i$ is arranged as an optical camera system or a depth-sensing camera to acquire an image of the patient when in the examination region between X-ray source and X-ray detector. On this image, image processing is performed such as image or pattern recognition to extract an estimate for applicable patient characteristics weight and/or height, or the extractor estimate for the weight or height of the patient. Priors used for this estimate may include in particular known geometrical relationships such as source XD-to-detector XD distance to estimate height and thickness of patient PAT and hence their body mass/weight.

According to a different embodiment the sensor system includes RFID (radio frequency identification) readers and one or more RFID tags. The one or more RFID tags are applied to the patient beforehand. The tag(s) encode some or all patient characteristics or at least include a reference code for these data for retrieval from the HRM. Once the patient is in the examination room or resides in the examination region, the patient characteristic data is acquired by the RFID reader through interrogation of the RFID tag(s) and the data is then forwarded to the input port IN.

In yet another embodiment, the sensors $SS_i$ include X-ray sensitive sensors arranged in the examination room. These sensors are capable of detecting x-radiation scattered off the patient. The amount of scatter detected provides an indication of the body mass of the patient and hence as to whether the correct tube voltage is used for exposure. "Correct" means a voltage relative high enough achieve a given image quality. The ratio between scatter and body mass may be learned experimentally from previously acquired training data.

In yet another embodiment, the sensor system $SS_i$ includes an electro-mechanical sensor, such as a digital scale mounted on, or in the floor underneath the examination region for the patient to step on so that the body mass of the patient PAT can be readily established and provided as a patient PAT characteristic reading to the input port IN of the module M. The scale may also be mounted in an examination table.

The different embodiments of the sensor system SSi described above may be used singly or in combination, as required. The information provided by the sensor system SSi, such as the image recognition embodiment, may be used to establish an identity of the patent PAT. It will be appreciated that the various sensor system SSi embodiments described above can be used whilst an imaging is on-going so that the remedial action by safety enforcer SE, can be applied during the imaging if required. Alternatively, the sensors are used up-front once prior to imaging although this is not the preferred embodiment. Indeed, in a preferred embodiment, the proposed safety system XSYS is configured as dynamic system, capable of quasi-real time operation. Specifically, it is envisaged that the sensor system SSi operates in a loop at a fixed or adjustable sample frequency to acquire a stream of sensor readings. The compliance checker checks repeatedly for compliance with the current safety protocol in synchrony with the sample frequency. The same repeated operation in synchrony with the sampling frequency is also envisaged for a protocol changer PC to dynamically change or reconfigure the existing protocol if the sensor readings indicate change of the imaging situation. In particular a change over from one patient to another can be detected and the protocol can be exchanged or re-configured accordingly by the protocol changer PC based on the new characteristics of the following patient.

The sensor system $SS_i$, in cooperation with the compliance checker CC and protocol changer PC, may not only detect whether a patient has changed for another but also whether a given patient has changed imaging position. The change of position of the same patient may require a safety protocol change because for different body parts or organs different imaging settings are usually called for.

The compliance checker CC, as mentioned briefly above, may also include a logger (not shown) that logs all imaging activity performed in respect of a given patient PAT. This allows establishing the number of X-ray shots per unit time. The number of allowed X-ray exposures per unit time may be another parameter in the imaging protocol that is checked against for compliance by the checker CC. In other words, the exposures ("shots") per position or patient are linked or integrated into the safety protocol by protocol changer PC for better reconciliation with existing imaging work flows. If a newly requested X-ray exposure would result in exceeding the allowable number of X-ray exposures for the specific patient, the safety action is carried out and/or the alert signal is issued. Integration or linking-in of the maximum number of X-ray exposures for the patient may be implemented electronically as a certificate that prescribes the maximum number of shots or dose per patient.

As a further refinement, the compliance checker CC may operate in a fuzzy mode, and differentiates in respect of safety protocol violations. A score system can be used to assess severity of the violation. The alert signal or the control signal is only issued if the score exceeds a safety threshold. Minor violations can be ignored.

Figure 3:
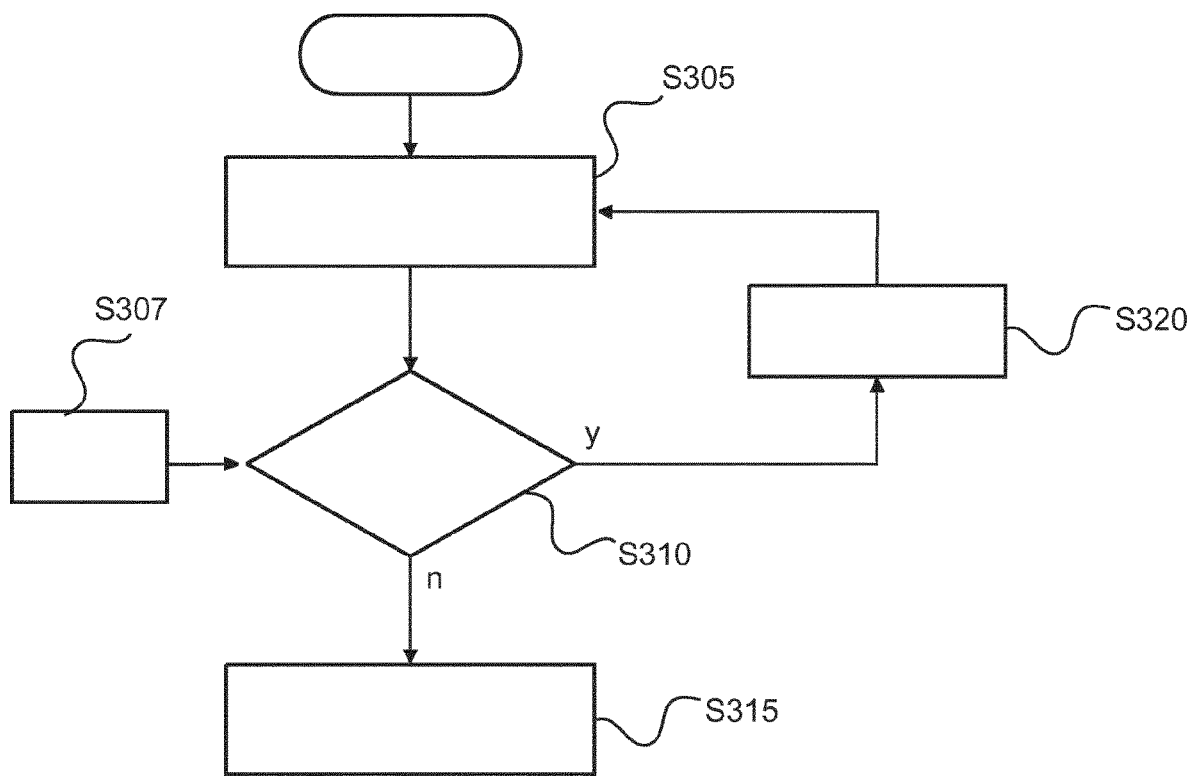
FIG. 3 shows a flow chart of a method for supporting X-ray imaging.

Reference is now made to FIG. 3 which shows a flow chart of a method of supporting safe X-ray imaging. The method underlies and summarizes operation of the system XSYS as per FIG. 1. However, it will be understood that the following method steps may also be understood as a teaching in its own right.

At step S305 an imaging request is received to perform an X-ray exposure of patient PAT. The request includes or is associated with, in particular, patient characteristics, imaging settings and the image task to be performed. The image task relates to the organ or region of interest to be imaged (e.g., chest X-ray).

In step S310 the imaging settings included in or associated with the request are checked against an imaging safety protocol for the patient. The checking operation concludes with a safety compliance result which indicates whether or not the requested imaging, in particular the X-ray exposure, is in compliance with the requirements/imaging settings encoded in the imaging safety protocol.

If the result indicates that there is no violation (that is, there is compliance), method flow proceeds to step S315 and the requested X-ray exposure is allowed to proceed or is allowed to continue (as the case may be), with the associated imaging settings.

If however, at step S310, it is established that there is a violation, in other words, that there is a miss-match between the imaging settings for the requested X-ray exposure and the safety requirements as per the safety protocol, an alert signal and/or an initiating control signal is issued at step S320. The control signal is to effect a safety action to at least affect (in general reduce) the impact of the requested X-ray exposure. In particular, the objective is to reduce the dose as much as possible given the image quality required. The safety action may include disabling or locking down the X-ray system or parts thereof so that the requested exposure cannot commence or that an ongoing X-ray exposure is interrupted. The safety action may in particular include shutting down the whole imager.

Other safety actions envisaged at step S320 include re-collimating a collimator COL of the imager to change, in particular decrease a cross section of the X-ray beam. For the re-collimation, an image from the scout scan may be used to ascertain whether the region of interest (RO) still falls into narrower beam. Narrowing the beam XB reduces dose on bystanders and patient PAT.

Yet other safety actions envisaged include effecting moving the patient outside the X-ray beam, for instance where the patient resides on a motorized examination bed during the procedure and/or remedial action may include moving the X-ray source so that the patient is no longer exposed.

Yet other safety actions envisaged include adjusting the tube settings, including for instance reducing voltage or current of X-ray source, (current) filtration of beam to tune X-ray spectrum, selection of X-ray sources if the imager has multiple X-ray source, changing distance between X-ray source and object and/or between object and detector.

If it is an objective to ensure the image quality and the checking step at S310 finds that the preset image quality as per the safety protocol is not achieved, an appropriate action at S320 to take me be to change the tube settings or collimator settings so as to achieve this. In particular, this may entail increasing any one of tube voltage, current and exposure time and/or opening up the collimator to increase beam cross-section.

The safety actions can be performed to override user but it is preferable to complete the safety action after approval by user, eg when the dose is to be increased to ensure preset image quality. This can be done by producing a message on a display unit DU. The message includes the nature of the violation as found by the checking at step S310 and the safety action proposed. The message is configured to solicit approval by user, e.g. by displaying an interactive approval button widget on the screen of the display unit.

In one embodiment the compliance check at step S310 is ongoing even though a disabling control signal has been issued. Once compliance has been restored the imaging procedure is then allowed to resume. In addition or instead, the imaging may commence or continue once a suitable approval signal from a senior staff member is received at the input port. The approval signal may be issued by a suitable communication device such as a laptop, smart (mobile) phone, etc. through a suitable communication network coupled to the safety system as proposed herein.

The method may further include a step S307 of changing or reconfiguring the safety protocol, in response to receiving information in relation to the object, in particular patient characteristics (in particular, height, body mass, sex, age), patient identity etc. The information may also relate to a change from one patient to another or to a (e.g. angular) repositioning of the same patient. The information may be supplied direct by the user or is received from a remote data memory, such an electronic health record. In addition or instead, the information may be acquired through monitoring the examination region/patient through a sensor system. The sensor system includes: optical camera(s), RFID sensing, scales, X-ray sensors, and others.

The proposed safety protocol includes in one embodiment a log entry for the total amount of dose received by the specific patient in previous exposures. The protocol may also prescribe a limit for the patient on X-ray exposures per unit time (hours, days, etc.).

The method is envisaged in a preferred embodiment as a dynamic process, with ongoing monitoring through the sensors at a suitable sampling frequency and repeated checking for compliance at step 310 based on the incoming data stream acquired by the sensors. In a second loop, the compliance check at step S310 is also repeated, each time the safety protocol is changed at step S307.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention. This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging system, comprising:
    an X-ray imager;
    an input interface for receiving a request to perform an X-ray exposure with an X-ray source of the X-ray imager to image an object;
    a compliance checker configured to check said request against an imaging safety protocol for said object to produce a safety compliance result, wherein checking by the compliance checker is based on information that identifies the object, wherein the imaging safety protocol prescribes a maximum number of allowable X-ray exposures per unit time for the object; and
    a safety enforcer configured to issue, based on the safety compliance result, at least one of an alert signal and a control signal to initiate a safety action that affects an impact of the X-ray exposure on the object.

2. The imaging system according to claim 1, wherein said safety action includes at least one of locking down or shutting down the X-ray imager, adjusting a voltage or current of the X-ray source, operating a collimator of the X-ray imager to change X-ray exposure, and performing a relative motion between the object and X-ray source.

3. The imaging system according to claim 1, comprising a protocol changer configured to change said safety protocol in response to receiving further information on said object or on a change in relation to said object.

4. The imaging system according to claim 1, wherein said information is provided by one or more sensors that are operative to perform one or more measurements in relation to said object.

5. The imaging system according to claim 1, comprising a user interface for receiving said information from a user.

6. The imaging system according to claim 1, comprising a communication interface for receiving said information from a remote data supplier equipment.

7. The imaging system according to claim 1, wherein the imaging safety protocol further prescribes at least one of maximum or minimal voltage, and amperage of the X-ray source.

8. The imaging system according to claim 1, wherein the maximum number of allowable X-ray exposures per unit time is a maximum number of allowable X-ray exposures per unit time for a given patient to be imaged or being imaged.

9. A method of supporting X-ray imaging, comprising:
    receiving a request to perform an X-ray exposure with an X-ray source of an X-ray imager to image an object;
    checking said request against an imaging safety protocol for said object to produce a safety compliance result, wherein the checking is based on information that identifies the object, wherein the imaging safety protocol prescribes a maximum number of allowable X-ray exposures per unit time for the so identified object; and
    issuing, based on the safety compliance result, at least one of an alert signal and a control signal to initiate a safety action that affects an impact of the X-ray exposure on the object.

10. The method according to claim 9, further comprising changing said safety protocol in response to receiving information on said object or on a change in relation to said object.

11. A non-transitory computer-readable medium having one or more executable instructions stored thereon which, when executed by at least one processor, cause the at least one processor to perform a method for supporting X-ray imaging, the method comprising:
    receiving a request to perform an X-ray exposure with an X-ray source of an X-ray imager to image an object;
    checking said request against an imaging safety protocol for said object to produce a safety compliance result, wherein the checking is based on information that identifies the object, wherein the imaging safety protocol prescribes a maximum number of allowable X-ray exposures per unit time for the so identified object; and
    issuing, based on the safety compliance result, at least one of an alert signal and a control signal to initiate a safety action that affects an impact of the X-ray exposure on the object.

12. The non-transitory computer-readable medium according to claim 11,
    wherein the method further comprises changing said safety protocol in response to receiving information on said object or on a change in relation to said object, and
    wherein the maximum number of allowable X-ray exposures per unit time is a maximum number of allowable X-ray exposures per unit time for a given patient to be imaged or being imaged.

* * * * *